United States Patent [19]

Shaw et al.

[11] Patent Number: 5,545,714
[45] Date of Patent: Aug. 13, 1996

[54] OXIDATION OF DIMERCAPTANS TO ORGANIC DISULFIDE POLYMERS

[75] Inventors: James E. Shaw; William E. Sattich; Howard F. Efner, all of Bartlesville, Okla.

[73] Assignee: Phillips Petroleum Company, Bartlesville, Okla.

[21] Appl. No.: 450,828

[22] Filed: May 25, 1995

Related U.S. Application Data

[62] Division of Ser. No. 290,666, Aug. 15, 1994, Pat. No. 5,464,931.

[51] Int. Cl.$^6$ ............................................. C08G 75/04
[52] U.S. Cl. ........................................ 528/374; 528/375
[58] Field of Search ............................ 528/374, 375

[56] References Cited

U.S. PATENT DOCUMENTS

| | | | |
|---|---|---|---|
| 3,625,925 | 12/1971 | Oswald | 260/79 |
| 4,163,832 | 8/1979 | Oswald | 528/76 |
| 5,206,439 | 4/1993 | Shaw | 568/21 |
| 5,232,623 | 8/1993 | Shaw | 252/183.13 |
| 5,283,368 | 2/1994 | Shaw | 568/45 |

OTHER PUBLICATIONS

Tanaka et al. Tetrahedron, 44(11), 3241–3249, 1988.

Primary Examiner—Marion E. McCamish
Assistant Examiner—Helen F. Lee
Attorney, Agent, or Firm—Lucas K. Shay

[57] ABSTRACT

A process for preparing an organic disulfide polymer such as polyethylene disulfide which is used in batteries comprises contacting a dimercaptan such as 1,2-ethanedithiol with elemental sulfur using a mixture of a basic compound such as NaOH and an ethoxylated alcohol such as Union Carbide's TERGITOL® 15-S-7 having the formula of $R^2O(CH_2CH_2O)_7H$ as catalyst wherein the dimercaptan is present in excess amount to effect the preparation of the disulfide polymer.

23 Claims, No Drawings

OXIDATION OF DIMERCAPTANS TO ORGANIC DISULFIDE POLYMERS

This application is a Division of application Ser. No. 08/290,666, filed Aug. 15, 1994, now U.S. Pat. No. 5,464,931.

FIELD OF THE INVENTION

The present invention relates to a process for oxidation of dimercaptans to produce organic disulfide polymers.

BACKGROUND OF THE INVENTION

Organic disulfide polymers are a class of important industrial compounds used commercially, for example, in battery applications and in high pressure lubricant applications.

Organic disulfide polymers can be prepared by polycondensation of a dihalide monomer with sodium disulfide in an aqueous solution. A trihaloalkane such as, for example, trichloropropane can also be added to the reaction medium to provide some degree of crosslinking of the disulfide polymers. However, this polycondensation process must be carried out in a suspension and the polymer thus-produced must be separated from the by-product sodium halide salts.

Organic disulfide polymers can also be prepared by oxidative polymerization of dithiols. For example, Japanese Application 49-104784 discloses the reaction of 1,2-ethanedithiol with oxygen in the presence of specific catalysts. The oxidation of 1,2-ethanedithiol can also be carried out with a halogen or hydrogen peroxide. However, these oxidative polymerization processes have some disadvantages. For instance, an oxidative polymerization using hydrogen peroxide is very exothermic and addition of hydrogen peroxide must therefore be slow. There is therefore an ever-increasing need to develop a better process for the preparation of an organic disulfide polymer.

SUMMARY OF THE INVENTION

An object of the present invention is to provide a process for the oxidation of a dimercaptan. Also an object of the present invention is to provide a process for preparing an organic disulfide polymer. Another object of the present invention is to provide a process for the oxidation of a dithiol using sulfur. An advantage of the present invention is that the present invention process is not exothermic. Another advantage is that the dimercaptan is oxidized by sulfur without introducing air or oxygen. Yet another advantage is that the by-product of the present invention is hydrogen sulfide which can be easily separated from the reaction mixture. Other objects, advantages, or features will become more apparent as the invention is more fully disclosed hereinbelow.

According to a first embodiment of the present invention, a process for the oxidation of a dimercaptan is provided which comprises contacting a dimercaptan, in the presence of a catalyst comprising an alkoxylated compound and a base, with sulfur under conditions sufficient to oxidize the dimercaptan wherein said dimercaptan catalyst, and sulfur are each present in an effective amount to effect the oxidation.

According to a second embodiment of the present invention, a process which can be used to produce an organic disulfide polymer is provided wherein the process comprises contacting a dithiol, in the presence of a catalyst which comprises an alkoxylated compound and a base, with elemental sulfur under conditions effective to oxidize the dithiol to a disulfide polymer wherein the dithiol, catalyst, and sulfur are each present in an effective amount to oxidize the dithiol to the disulfide polymer.

DETAILED DESCRIPTION OF THE INVENTION

According to the first embodiment of the invention, a process for oxidizing a dimercaptan is provided which comprises contacting a dimercaptan, in the presence of a catalyst, with elemental sulfur. Any dimercaptan that can be oxidized by elemental sulfur such as, for example, a primary or a secondary dimercaptan, can be used in the present invention. Examples of suitable dimercaptans include, but are not limited to, 1,2-ethanedithiol, 1,2-propanedithiol, 1,3-propanedithiol, 1,10-decanedithiol, dipentene dimercaptan, ethylcyclohexyl dimercaptan, 1,4-benzenedithiol, 1,3-benzenedithiol, 1,2-benzenedithiol, and combinations of two or more thereof. The presently preferred dimercaptans are 1,2-ethanedithiol and 1,3-propanedithiol because the oxidation products thereof have important industrial applications.

The catalyst useful in the present invention is a composition comprising an alkoxylated compound and a basic compound. The alkoxylated compound is selected from the group consisting of an alkoxylated alcohol, an alkoxylated mercaptan, and combinations thereof.

The base useful as a component of the present invention is a basic compound that can effect the oxidation of a dimercaptan when used with an alkoxylated compound and can be an organic or an inorganic base, or mixtures thereof. Suitable bases include, but are not limited to tetramethylammonium hydroxide, tetraethylammonium hydroxide, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, sodium phenoxide, sodium bisulfide, sodium sulfide, barium phenoxide, calcium phenoxide, RONa, RSNa, and mixtures of any two or more thereof; where R is a $C_1$–$C_{18}$ alkyl radical. Presently, an inorganic base is preferred because of availability and low cost of inorganic bases. Among the inorganic bases, sodium hydroxide is preferred because it is readily available and inexpensive.

The alkoxylated alcohol useful in the present invention has a general formula of $R^1O[CH_2CH(R^2)O]_nH$ where $R^1$ is a $C_1$–$C_{20}$ hydrocarbyl radical selected from the group consisting of alkyl radical, alkylaryl radical, aryl radical, cycloalkyl radical and alkenyl radical; preferably $R^1$ is a $C_6$–$C_{18}$ alkyl radical. Most preferably $R^1$ is a $C_{10}$–$C_{16}$ alkyl radical; $R^2$ is selected from the group consisting of hydrogen, $C_1$–$C_{16}$ alkyl radicals, $C_2$–$C_{16}$ alkenyl radicals, and combinations thereof; and n is a number of from 1 to about 20, preferably from about 2 to about 12, most preferably from 5 to 10. Generally $R^2$ can contain from 0 to about 16 carbon atoms. Preferably $R^2$ is a hydrogen or a $C_1$–$C_3$ alkyl radical. Most preferably $R^2$ is hydrogen. An example of suitable alkoxylated alcohol is TERGITOL® 15-S-7 which is an ethoxylated alcohol manufactured and marketed by Union Carbide Corporation, and has the formula of $R^1O(CH_2CH_2O)_7H$ where $R^1$ is a secondary alkyl radical having 11–15 carbon atoms and 7 is an averaged number of the ethylene oxide units. Another example is an ethoxylated phenol having the same number of ethylene oxide units. Other alkoxylated alcohols are also available from Union Carbide Corporation.

The alkoxylated mercaptan useful in the present invention has a general formula of $R^1S[CH_2CH(R^2)O]_nH$ where $R^1$ and $R^2$ are the same as those described above. An example of an alkoxylated mercaptan is an ethoxylated mercaptan having the formula of $R^1S(CH_2CH_2O)_7H$ where $R^1$ is primarily a tertiary dodecyl group and 7 is an averaged number of ethylene oxide units. This ethoxylated mercaptan is a surfactant commercially available from Phillips Petroleum Company, Bartlesville, Okla. under the trade name AQUA-CLEEN® II. Another example is an ethoxylated thiophenol having the same number of ethylene oxide units. Other alkoxylated mercaptans are also available from Phillips Petroleum Company.

The weight ratio of the alkoxylated alcohol or alkoxylated mercaptan to base is the ratio that can effect the oxidation of a mercaptan and can vary widely, preferably from about 1:1 to about 999:1, more preferably from about 5:1 to about 100:1, and most preferably from 10:1 to 50:1 for best results.

The present composition useful as catalyst can be made by any mixing method known to one skilled in the art such as, for example, properly mixing the components in the ratio described above employing any suitable mixing means such as shaking or stirring under a sufficient condition to prepare the composition.

While the oxidation of mercaptans by elemental sulfur can be depicted as $R^3SH+R^4SH+S \rightarrow R^3S\text{-}SR^4+H_2S$, the oxidation of dimercaptans by elemental sulfur to desired organic disulfide polymers can depicted as $(q+1)HSR^4SH+qS \rightarrow HS\text{-}(R^4\text{-}S\text{-}S)_q R^4SH+qH_2S$; where $R^3$ and $R^4$ can be the same or different and are each hydrocarbyl radicals having about 1 to about 20 carbon atoms and are selected from the group consisting of alkyl, aryl, cycloalkyl, alkylaryl, and alkenyl radicals. Preferably $R^3$ and $R^4$ are each an alkyl radical having 2 to 15 carbon atoms. The q is a number of 1 to about 1000. Preferably q is from about 5 to about 500, and most preferably from 10 to 200. The oxidation can be carried out in any suitable reaction vessel. The choice of reaction vessel is a matter of preference to those skilled in the art.

The catalyst also can be formed in-situ by adding a base and either an alkoxylated alcohol or an alkoxylated mercaptan before or during the contacting of mercaptans and elemental sulfur. It can also be prepared by heating the mixture of the alkoxylated alcohol or alkoxylated mercaptan and the base at a temperature in the range of from about 40° C. to about 150° C., preferably from 60° C. to 100° C. for from about 10 minutes to about 5 hours, preferably from 30 minutes to 2 hours. The heating is preferably carried out under an inert gas such as nitrogen and can be under any pressure, preferably under about 1 atmosphere to about 2 atmospheres.

According to the first embodiment of the invention, suitable conditions for the contacting of dimercaptans with elemental sulfur are those conditions that can effectively oxidize the dimercaptans with the sulfur. Generally the conditions can include a temperature in the range of from about 20° C. to about 250° C., preferably from about 30° C. to about 200° C., and most preferably from 40° C. to 150° C. and a time of from about 1 minute to about 10 hours, preferably about 2 minutes to about 6 hours, and most preferably from 3 minutes to 3 hours. The pressure can vary widely from less than about 1 atmosphere to about 30 atmospheres, preferably from about 1 atmosphere to about 15 atmospheres, and most preferably from 1 atmosphere to 5 atmospheres.

Generally, one of the reactants, either dimercaptan or sulfur, can be slowly added to the other reactant in the presence of the catalyst described above. It is generally preferred that sulfur be added to the dimercaptan because of the desired excess dimercaptan in the reaction medium. The sulfur, upon addition, readily dissolves in the solution. Mixing of the solution and/or operating at higher than ambient temperatures will enhance the reaction rate. The amount of sulfur added depends on the desired oxidized product. Generally, each mole of sulfur is contacted with or added to about 1 to about 50, preferably about 1.5 to about 10, and most preferably about 2 moles of dimercaptans and about 1 mole of hydrogen sulfide will be released per mole of sulfur reacted. The weight of the catalyst or the weight of the alkoxylated compound and basic compound as a percentage of the weight of dimercaptan can be any percentage that is effective to oxidizing a dimercaptan and is generally in the range of from 0.01 to 50%, preferably about 0.1 to 10%, and most preferably 0.5 to 5%.

Following completion of the reaction, residual hydrogen sulfide is generally removed from the oxidized product by either an inert gas purge or by vacuum stripping. When using an inert (or non-reactive) gas purge, the preferable gases are nitrogen and air.

Following the removal of most of the residual hydrogen sulfide, the oxidized product can be further separated, purified, recovered, or combinations thereof, as necessary. This may be done by any conventional means such as, for example, filtration or distillation.

According to the second embodiment of the present invention, a process for preparing an organic disulfide polymer is provided. The process comprises contacting a dithiol having the formula of $HSR^4SH$ with elemental sulfur under conditions effective to achieve the synthesis of an organic disulfide polymer. The invention process can be depicted as $(q+1)HSR^4SH+qS \rightarrow HS\text{-}(R^4\text{-}S\text{-}S)_q R^4SH+qH_2S$ wherein the scope of q and $R^4$ is the same as that disclosed in the first embodiment of the present invention.

The specific and illustrative conditions of the second embodiment of the invention are generally the same as disclosed above in the first embodiment of the invention.

The oxidation of dimercaptans and the preparation of an organic disulfide polymer can also be carried out in the presence of a solvent. The term solvent as used herein refers to a fluid possessing solvation properties and which may also partake in the reaction as part of a reaction intermediate. Suitable solvents include protic solvents such as water and alcohols and also aprotic solvents such as hydrocarbons and ethers. Specific examples of alcohols include, but are not limited to, methanol, ethanol, n-propanol, isopropanol, butanols, pentanols, and mixtures thereof. Specific examples of aprotic solvents include pentane, hexane, diethyl ether, tetrahydrofuran, and mixtures thereof. The most preferred solvent is methanol because of its availability and ease to use.

The weight ratio of solvent, if present, to the weight of the dimercaptan to a great extent dependent upon the available process equipment and within the discretion of one possessing ordinary skill in the art. Generally, it can be in the range of from about 100:1 to about 0.1:1, preferably from 10:1 to 1:1.

The process of both embodiments of the invention can also be carried out continuously. For example, the contacting of mercaptans with elemental sulfur in the process of the above-disclosed composition can be done by employing continuous stirred tank reactors connected in series, packed columns or towers in which the invention catalyst is supported on a solid support, and other continuous flows that are readily within the realm of one skilled in the art.

The desired organic disulfide polymer can be separated from the process mixture which contains unreacted dimercaptan, catalyst, and solvent, if present, by any conventional means such as, for example, filtration or distillation. The unreacted dimercaptan and catalyst can be recycled to produce additional disulfide polymer.

The following examples are provided to further illustrate the practice of the invention and are not intended to limit the scope of the invention or the claims.

other catalysts replaced NaOH and TERGITOL® 15-S-7. GC samples were taken immediately after the sulfur was added and after 15 minutes. The catalysts and their amounts are as follows:

Run 2 0.10 ml (0.073 g) triethylamine

Run 3 0.25 g of 20% tetramethylammonium hydroxide in methanol

Run 4 0,052 g 50% aqueous NaOH

Run 5 0.33 g of TERGITOL® 15-S-7

Run 6 0,386 g of 6.7% NaOH in methanol

As can be seen in Table I below, the catalyst used in the invention process (Run 1) produced essentially only organic disulfide, especially immediately after the mercaptan was contacted with sulfur.

TABLE I

| | | Di-n-Propyl Disulfide Runs | | | |
|---|---|---|---|---|---|
| | | Relative % of Disulfide and Trisulfide | | | |
| | | Immediately after Sulfur Added | | 15 Minutes after Sulfur Added | |
| Run | Catalyst | % Disulfide | % Trisulfide | % Disulfide | % Trisulfide |
| 1 | NaOH-TERGITOL® 15-S-7 | 98.7 | 1.3 | 99.8$^{a,b}$ | 0.2$^{a,b}$ |
| 2 | triethylamine | 53.3 | 46.7 | 82.0 | 18.0 |
| 3 | tetramethylammonium hydroxide | 75.3 | 24.7 | 98.9 | 1.1 |
| 4 | NaOH only | almost no reaction | almost no reaction | 40.9 | 59.1 |
| 5 | TERGITOL® 15-S-7 only | no reaction | no reaction | no reaction | no reaction |
| 6 | NaOH-methanol | 20.8 | 79.2 | 41.4$^a$ | 58.6$^a$ |

$^a$Values after 10 minutes rather than 15.
$^b$After 20 minutes, the values were 99.9 and 0.1%.

EXAMPLE I

This example illustrates the selectivity of the catalyst employed in the invention process to produce organic disulfide.

To a 100 ml, 3-necked flask equipped with thermowell, magnetic stir bar, and condenser was added 0.052 g of 50% aqueous NaOH, 0.344 g of TERGITOL® 15-S-7 (Union Carbide), and 9.50 g of n-propyl mercaptan (100% excess). This mixture was heated to 50° C. with stirring. Then 1.00 g of sulfur (powdered flowers of sulfur) was added in portions over 1–2 minutes. There was immediate reaction and hydrogen sulfide was given off. Immediately after the sulfur was added, a 0.5 ml sample was taken for GC analysis. This was repeated after 10 minutes and 20 minutes. The only products were di-n-propyl disulfide, di-n-propyl trisulfide, and excess n-propyl mercaptan. The relative percentages of disulfide and trisulfide are given in Table I (Run 1).

For comparison purpose, five more runs were carried out. The reaction was carried out exactly the same way except

EXAMPLE II

This example illustrates the selectivity of the catalyst used in the invention process to produce organic disulfide.

To a 250 ml, 3-necked flask equipped with thermowell, magnetic stir bar, and condenser was added 0.30 g of 50% aqueous NaOH, 1.93 g of TERGITOL® 15-S-7 (Union Carbide), and 60.0 g of n-octyl mercaptan (100% excess). The mixture was heated to 50° C. with stirring. Then 3.3 g of sulfur (powdered flowers of sulfur) was added in portions over 4–5 minutes. Hydrogen sulfide was given off. Immediately after the sulfur was added, a 0.5 ml sample was taken for GC analysis. This was repeated after 15 minutes and 45 minutes. The only products were di-n-octyl disulfide, di-n-octyl trisulfide, and excess n-octyl mercaptan. The relative % of disulfide and trisulfide are given in Table II (Run 11).

Another run (Run 12) was carried out the same way except that triethylamine (0.50 ml, 0.36 g) replaced the NaOH-TERGITOL® 15-S-7 as catalyst. As Seen in Table II, even after 45 minutes, significant trisulfide was present when triethylamine was the catalyst.

TABLE II

| | Di-n-Octyl Disulfide Runs Relative % of Disulfide and Trisulfide | | | | | |
| --- | --- | --- | --- | --- | --- | --- |
| | Immediately after Sulfur Added | | 15 Minutes after Sulfur Added | | 45 Minutes after Sulfur Added | |
| Run Catalyst | % Disulfide | % Trisulfide | % Disulfide | % Trisulfide | % Disulfide | % Trisulfide |
| 11 NaOH-TERGITOL® 15-S-7 | 99.5 | 0.5 | 99.5[a,b] | 0.5[a,b] | 100.0 | 0 |
| 12 triethylamine | 57.4 | 42.6 | 63.5 | 36.5 | 72.8 | 27.2 |

[a] Values after 10 minutes rather than 15.
[b] After 20 minutes, the values were 99.9 and 0.1%.

EXAMPLE III

This example illustrates the preparation of polyethylene disulfide using the invention process.

To a 100 ml flask equipped with thermowell magnetic stir bar, and condenser was added 0.14 g of 50% aqueous NaOH, 0.82 g of TERGITOL®15-S-7 (Union Carbide), and 23.5 g of 1,2-ethanedithiol. There was a 100% excess of ethanedithiol relative to the amount of elemental sulfur used. The mixture was heated to 50° C. with stirring. Then 4.0 g of elemental sulfur (powdered flowers of sulfur) was added in portions over about 5 minutes with stirring. Hydrogen sulfide was evolved. After the addition was complete, the reaction mixture was stirred for 1 hour at 50° C. A white solid precipitated out during this time.

The reaction mixture was cooled and 50 ml of n-hexane was added. A slurry was prepared which was suction filtered using a Buchner funnel and water aspirator. The solid product in the funnel was washed with 50 ml water and then with 100 ml of acetone. The pure white solid was allowed to dry in the air at room temperature. The weight was 11.4 g (99.1% yield based on elemental sulfur used). The infrared spectrum (KBr pellet) was identical to that of an authentic sample prepared by $H_2O_2$ oxidation of ethanedithiol. Combustion analysis of the product showed that it contained 26.01% carbon (C) and 4.44% hydrogen (H) whereas theoretical values are 26.06% C and 4.37% H. The sulfur content is measured by difference and was 69.55% (theoretical value is 69.57%). The melting point range was 160° C.–166° C. which compared favorably with that of the authentic sample (159.5° C.–165.6° C.).

Another run was carried out the same way except that after filtration the product in the funnel was washed with 25 ml of hexane, 50 ml of methanol, 50 ml of water, and lastly 100 ml of methanol. After drying in the air at room temperature, polyethylene disulfide was obtained in 100% yield as a white solid. Physical properties were essentially the same as those described above. Based on C and H combustion analyses, the sulfur content (by difference) was 68.69% (theoretical 69.57%).

EXAMPLE IV

This example illustrates the invention process for producing a polyethylene disulfide polymer using methanol as solvent.

To a 250 ml flask equipped with thermowell, magnetic stir bar, and condenser with $N_2$ inlet on top was added 0.14 g of 50% aqueous NaOH, 0.82 g of TERGITOL® 15-S-7 (Union Carbide), 23.5 g of 1,2-ethanedithiol (100% excess) and 40 g of methanol. The mixture was heated to 45°–50° C. with stirring, and 4.0 g of sulfur (powdered flowers of sulfur) was added in portions over 8 minutes with stirring. When the sulfur addition was almost complete, the reaction mixture started to turn milky white due to polymer formation. The mixture was stirred for 1 hour at 45°–50° C. The mixture was cooled to room temperature and then suction filtered using a Buchner funnel and water aspirator. The polymer in the funnel was washed with 200 ml of methanol. After drying in the air at room temperature, 11.3 g (98.3%) of polyethylene disulfide was obtained as a white powder. The infrared spectrum was identical to that of an authentic sample. It was noted that throughout the whole procedure, the polymer was always a finely divided solid which was easy to handle.

Advantages of the above procedure using methanol as solvent include, but are not limited to: (1) the polymer is finely divided and easy to handle; a white powder resulted; and (2) after the polymer was filtered out of the reaction mixture, the filtrate contained the excess 1,2-ethanedithiol and the methanol, NaOH, and TERGITOL®, so the filtrate can be recycled for production of more polymer. All that needs to be done is to add additional 1,2-ethanedithiol to the filtrate and then additional sulfur.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed is:

1. A process for oxidation of a dimercaptan having the formula of $HSR^4SH$ comprising contacting said dimercaptan, in the presence of a catalyst, with sulfur wherein $R^4$ is a hydrocarbyl radical having 1 to about 20 carbon atoms and said catalyst comprises a base and an alkoxylated compound selected from the group consisting of an alkoxylated alcohol, an alkoxylated mercaptan, and mixtures thereof.

2. A process according to claim 1 wherein $R^4$ is a hydrocarbyl radical having 2 to about 15 carbon atoms.

3. A process according to claim 1 wherein said dimercaptan is 1,2-ethanedithiol.

4. A process according to claim 1 wherein said base is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, potassium carbonate, sodium phenoxide, sodium bisulfide, sodium sulfide, barium phenoxide, calcium phenoxide, RONa, RSNa, and mixtures thereof wherein R is a $C_1$–$C_{18}$ alkyl radical.

5. A process according to claim 1 wherein said base is sodium hydroxide.

6. A process according to claim 1 wherein said alkoxylated alcohol has a formula of $R^1O[CH_2CH(R^2)O]_nH$ wherein $R^1$ is a hydrocarbyl radical selected from the group consisting of alkyl radical, alkylaryl radical, aryl radical, cycloalkyl radical and alkenyl radical; $R^2$ is selected from the group consisting of hydrogen, $C_1$–$C_{16}$ alkyl radical, $C_2$–$C_{16}$ alkenyl radical, and combinations thereof; and n is a number of 1 to about 20.

7. A process according to claim 6 wherein $R^1$ is a $C_6$–$C_{18}$ alkyl radical; $R^2$ is selected from the group consisting of hydrogen, a $C_1$–$C_3$ alkyl radical, and combinations thereof; and n is from about 2 to about 12.

8. A process according to claim 6 wherein $R^1$ is a $C_{10}$–$C_{16}$ alkyl radical, $R^2$ is hydrogen and n is from 5 to 10.

9. A process according to claim 6 wherein said alkoxylated alcohol is an ethoxylated alcohol having the formula of $R^1O(CH_2CH_2O)_7H$, wherein $R^1$ is a secondary alkyl radical having 11 to 15 carbon atoms and 7 is the average moles of ethylene oxide in the molecule.

10. A process according to claim 1 wherein said alkoxylated mercaptan has a formula of $R^1S[CH_2CH(R^2)O]_nH$ wherein $R^1$ is a hydrocarbyl radical selected from the group consisting of alkyl radical, alkenyl radical, alkylaryl radical, aryl radical and cycloalkyl radical; $R^2$ is selected from the group consisting of hydrogen, $C_1$–$C_{16}$ alkyl radical, $C_2$–$C_{16}$ alkenyl radical, and combinations thereof; and n is a number of from 1 to about 20.

11. A process according to claim 10 wherein $R^1$ is a $C_6$–$C_{18}$ alkyl radical; $R^2$ is selected from the group consisting of hydrogen, a $C_1$–$C_3$ alkyl radical, and combinations thereof; and n is from about 2 to about 12.

12. A process according to claim 10 wherein $R^1$ is a $C_1$–$C_3$ alkyl radical, $R^2$ is hydrogen, and n is from 5 to 10.

13. A process according to claim 10 wherein said alkoxylated mercaptan is an ethoxylated mercaptan surfactant having the formula of $R^1S(CH_2CH_2O)_7H$, wherein $R^1$ is a tertiary dodecyl radical and 7 is the average moles of ethylene oxide in the molecule.

14. A process according to claim 1 wherein said catalyst comprises sodium hydroxide as a base and an ethoxylated alcohol having the formula of $R^1O(CH_2CH_2O)_7H$ wherein $R^1$ is a secondary alkyl radical having 11 to 15 carbon atoms and 7 is the average moles of ethylene oxide in the molecule.

15. A process according to claim 1 wherein said catalyst comprises sodium hydroxide and an ethoxylated mercaptan surfactant having the formula of $R^1S(CH_2CH_2O)_7H$ wherein $R^1$ is a tertiary dodecyl radical and 7 is the average moles of ethylene oxide in the molecule.

16. A process according to claim 1 wherein said process is carried out in the presence of a solvent.

17. A process according to claim 16 wherein said solvent is selected from the group consisting of water, alcohols, hydrocarbons, ethers, and mixtures thereof.

18. A process according to claim 16 wherein said solvent is methanol.

19. A process according to claim 16 wherein said dimercaptan is present in an amount of about 2 moles of said dimercaptan per mole of element sulfur.

20. A process according to claim 1 wherein said dimercaptan is present in an amount of about 2 moles of said dimercaptan per mole of elemental sulfur.

21. A process for oxidation of a dimercaptan having the formula of $HSR^4SH$ comprising contacting said dimercaptan, in the presence of a catalyst, with sulfur wherein said catalyst comprises a base and an alkoxylated alcohol wherein:

$R^4$ is a hydrocarbyl radical having 2 to about 15 carbon atoms;

said base is selected from the group consisting of tetramethylammonium hydroxide, tetraethylammonium hydroxide, tetrapropylammonium hydroxide, tetramethylammonium bisulfide, tetraethylammonium bisulfide, lithium hydroxide, sodium hydroxide, potassium hydroxide, calcium hydroxide, magnesium hydroxide, sodium bicarbonate, sodium carbonate, sodium oxide, magnesium oxide, calcium oxide, calcium carbonate, potassium carbonate, sodium phenoxide, sodium bisulfide, sodium sulfide, barium phenoxide, calcium phenoxide, RONa, RSNa, and mixtures thereof wherein R is a $C_1$–$C_{18}$ alkyl radical; and said alkoxylated alcohol has a formula of $R^1O[CH_2CH(R^2)O]_nH$ wherein $R^1$ is a hydrocarbyl radical selected from the group consisting of alkyl radical, alkylaryl radical, aryl radical, cycloalkyl radical and alkenyl radical; $R^2$ is selected from the group consisting of hydrogen, $C_1$–$C_{16}$ alkyl radical, $C_2$–$C_{16}$ alkenyl radical, and combinations thereof; and n is a number of 1 to about 20.

22. A process according to claim 21 wherein said dimercaptan is 1,2-ethanedithiol, and said catalyst comprises sodium hydroxide and an ethoxylated alcohol having the formula of $R^1O(CH_2CH_2O)_7H$ wherein $R^1$ is a secondary alkyl radical having 11 to 15 carbon atoms and 7 is the average moles of ethylene oxide in the molecule.

23. A process for oxidation of 1,2-ethanedithol comprising contacting said 1,2-ethanedithol with elemental sulfur in the presence of a catalyst at a temperature in the range of from 50° C. to 150° C. for 1 minute to 5 hours to form a product mixture; wherein said catalyst is prepared by heating sodium hydroxide and an ethoxylated alcohol having the formula $R^1O(CH_2CH_2O)_7H$ wherein $R^1$ is a secondary alkyl radical having 11 to 15 carbon atoms and 7 is the average moles of ethylene oxide in the molecule.

* * * * *